United States Patent
Gewehr et al.

(10) Patent No.: US 7,846,958 B2
(45) Date of Patent: *Dec. 7, 2010

(54) FUNGICIDAL USE

(75) Inventors: Markus Gewehr, Kastellaun (DE); Ingo Rose, Mannheim (DE); Bernd Müller, Frankenthal (DE); Eberhard Ammermann, Heppenheim (DE); Ann Orth, Langhorne, PA (US); Henry Van Tuyl Cotter, Raleigh, NC (US)

(73) Assignee: BASF SE, Ludwigshafen (DE)

( * ) Notice: Subject to any disclaimer, the term of this patent is extended or adjusted under 35 U.S.C. 154(b) by 749 days.

This patent is subject to a terminal disclaimer.

(21) Appl. No.: 10/616,950

(22) Filed: Jul. 11, 2003

(65) Prior Publication Data

US 2004/0063793 A1  Apr. 1, 2004

(51) Int. Cl.
A01N 43/64 (2006.01)
A01N 37/44 (2006.01)
A01N 37/12 (2006.01)
A01N 37/02 (2006.01)

(52) U.S. Cl. ........................ 514/383; 514/256; 514/399; 514/539; 514/317; 514/687; 514/546; 514/524; 514/619; 514/676

(58) Field of Classification Search ................. 504/116, 504/118; 424/405; 514/256, 399, 539, 317, 514/687, 546, 524, 619, 676
See application file for complete search history.

(56) References Cited

U.S. PATENT DOCUMENTS 6,127,570 A * 10/2000 Curtze et al. ................. 560/140
6,521,628 B1 * 2/2003 Cotter et al. ............. 514/258.1
6,696,497 B2 * 2/2004 Sieverding et al. .......... 514/687
6,734,202 B2 * 5/2004 Cotter et al. ................. 514/383

FOREIGN PATENT DOCUMENTS

EP  0897904  * 2/1999

* cited by examiner

*Primary Examiner*—Sabiha Qazi
(74) *Attorney, Agent, or Firm*—Novak Druce + Quigg LLP

(57) ABSTRACT

The use of benzophenones of the formula I

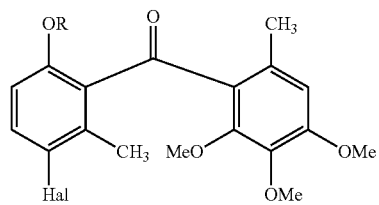

in which
R is hydrogen or $C_1$-$C_4$-alkyl and
Hal is fluorine, chlorine or bromine
for controlling *Pseudocercosporella herpotrichoides* in crop plants is described.

4 Claims, No Drawings

FUNGICIDAL USE

The present invention relates to the use of benzophenones of the formula I,

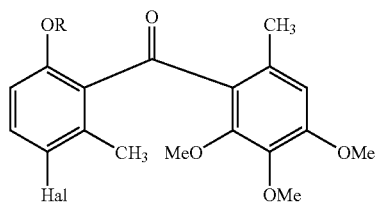

in which
R is hydrogen or $C_1$-$C_4$-alkyl and
Hal is fluorine, chlorine or bromine
for controlling *Pseudocercosporella herpotrichoides* in crop plants.

The benzophenones of the formula I are known from EP-A 727141, EP-A 897904 and EP-A 967196. The abovementioned publications also describe the fungicidal action of the benzophenones. The fungicidal action of the benzophenones against mildew infections (*Erysiphe graminis* forma *specialis tritici*) is explicitly mentioned. Furthermore, there have been reports of a fungicidal action of some benzophenones against rice blast (*Pyricularia orizae*) and apple scab (*Venturia inaequalis*). Mildew, rice blast and apple scab are different foliar diseases which occur in crop plants.

Surprisingly, it has now been found that the benzophenones of the formula I also have excellent activity against eyespot or stem break (*Pseudocercosporella herpotrichoides*). As indicated by the name, eyespot or stem break is a disease which affects mainly the stem of the crop plant. Wheat and barley, in particular, may be infected by eyespot.

Suitable benzophenones of the formula I are listed in table 1 below.

TABLE 1

| Comp. No. | R | Hal |
| --- | --- | --- |
| I.1 | $CH_3$ | Br |
| I.2 | H | Br |
| I.3 | $CH_3$ | Cl |
| I.4 | H | Cl |
| I.5 | $CH_3$ | F |
| I.6 | H | F |

Preferred benzophenones are the compounds 5-bromo-2',6-dimethyl-2,4',5',6'-tetramethoxybenzophenone (I.1); 5-bromo-2',6-di-methyl-2-hydroxy-4',5',6'-trimethoxybenzophenone (I.2); 5-chloro-2',6-dimethyl-2,4',5',6'-tetramethoxybenzophenone (I.3); 5-chloro-2',6-dimethyl-2-hydroxy-4',5',6'-trimethoxy-benzophenone (I.4) and in particular compound I.1.

The benzophenones I are applied by treating the fungi or the plants, seeds or materials to be protected from fungal infection, or the soil, with a fungicidally active amount of the active ingredients. Application can be effected both before and after infection of the materials, plants or seeds by the fungi.

In general, the fungicidal compositions comprise between 0.1 and 95, preferably between 0.5 and 90%, by weight of active ingredient.

When used in the protection of plants, the application rates are between 0.01 and 2.0 kg of active ingredient per ha, depending on the nature of the desired effect.

In the treatment of seeds, amounts of active ingredient of from 0.001 to 0.1 g, preferably from 0.01 to 0.05 g, are generally required per kilogram of seeds.

The compounds I can be converted into the customary formulations, for example solutions, emulsions, suspensions, dusts, powders, pastes and granules. The use form depends on the intended purpose in each case; in any case, it should ensure fine and uniform distribution of the compound according to the invention.

The formulations are prepared in a customary fashion, for example by extending the active ingredient with solvents and/or carriers, if appropriate using emulsifiers and dispersants, it also being possible to use other organic solvents as cosolvents if water is used as the diluent. Auxiliaries which can be used for this purpose are essentially: solvents such as aromatics (for example xylene), chlorinated aromatics (for example chlorobenzenes), paraffins (for example mineral oil fractions), alcohols (for example methanol, butanol), ketones (for example cyclohexanone), amines (for example ethanolamine, dimethylformamide) and water; carriers such as natural ground minerals (for example kaolins, clays, talc, chalk) and ground synthetic minerals (for example highly-dispersed silica, silicates); emulsifiers such as nonionic and anionic emulsifiers (for example polyoxyethylene fatty alcohol ether, alkylsulfonates and arylsulfonates) and dispersants such as lignosulfite waste liquors and methylcellulose.

Suitable surface-active substances are alkali metal salts, alkaline earth metal salts and ammonium salts of lignosulfonic acid, of naphthalenesulfonic acid, of phenolsulfonic acid, of dibutylnaphthalenesulfonic acid, alkylarylsulfonates, alkyl sulfates, alkylsulfonates, fatty alcohol sulfates and fatty acids, and their alkali metal and alkaline earth metal salts, salts of sulfated fatty alcohol glycol ether, condensates of sulfonated naphthalene and naphthalene derivatives with formaldehyde, condensates of naphthalene or naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Materials which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, for example dimethylformamide, dimethyl sulfoxide, N-methylpyrrolidone or water.

Powders, materials for spreading and dusts can be prepared by mixing or concomitantly grinding the active substances together with a solid carrier.

Granules, for example coated granules, impregnated granules and homogeneous granules, can be prepared by binding the active ingredients to solid carriers. Examples of solid carriers are mineral earths such as silica gel, silicic acids, silica gels [sic], silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers such as, for example, ammonium sulfate, ammonium phosphate, ammonium nitrate, ureas and products of vegetable origin, such as cereal meal, tree bark meal, wood meal and nutshell meal, cellulose powders and other solid carriers.

In general, the formulations comprise between 0.01 and 95% by weight, preferably between 0.1 and 90% by weight, of the active ingredient. The active ingredients are employed in a purity of from 90% to 100%, preferably 95% to 100% (according to NMR spectrum).

Examples of Formulations are:

I. 5 parts by weight of a compound according to the invention are mixed intimately with 95 parts by weight of finely divided kaolin. This gives a dust comprising 5% by weight of the active ingredient.

II. 30 parts by weight of a compound according to the invention are mixed intimately with a mixture of 92 parts by weight of pulverulent silica gel and 8 parts by weight of paraffin oil with which the surface of this silica gel has been sprayed. This gives a preparation of the active ingredient with good adhesion (active ingredient content 23% by weight).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (active ingredient content 9% by weight).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (active ingredient content 16% by weight).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (active ingredient content 80% by weight).

VI. 90 parts by weight of a compound according to the invention are mixed with 10 parts by weight of N-methyl-α-pyrrolidone, which gives a solution which is suitable for use in the form of microdrops (active ingredient content 90% by weight).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100 000 parts by weight of water and finely distributing it therein gives an aqueous dispersion comprising 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20 000 parts by weight of water gives a spray mixture comprising 0.1% by weight of the active ingredient.

IX. 10 parts by weight of the compound according to the invention are dissolved in 63 parts by weight of cyclohexanone, 27 parts by weight of dispersant (for example a mixture of 50 parts by weight of the adduct of 7 mol of ethylene oxide and 1 mol of isooctylphenol and 50 parts by weight of the adduct of 40 mol of ethylene oxide and 1 mol of castor oil). The stock solution is subsequently diluted by distributing in water to the desired concentration, for example to a concentration in the range of from 1 to 100 ppm.

The active ingredients can be used as such, in the form of their formulations or the use forms prepared therefrom, for example in the form of directly sprayable solutions, powders, suspensions or dispersions, emulsions, oil dispersions, pastes, dusts, materials for spreading, granules, by means of spraying, atomizing, dusting, spreading or pouring. The use forms depend entirely on the intended uses; in any case, they should guarantee the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of wetters, adhesives, dispersants or emulsifiers. However, it is also possible to prepare concentrates composed of active substance wetter, adhesive, dispersant or emulsifier and, if appropriate, solvent or oil, and such concentrates are suitable for dilution with water.

The active ingredient concentrations in the ready-to-use preparations can be varied within substantial ranges. In general, they are between 0.0001 and 10%. Frequently, low application. rates of compound I in the ready-to-use preparation frequently suffice, for example from 2 to 200 ppm. Ready-to-use preparations with active ingredient concentrations in the range of from 0.01 to 1% are likewise preferred.

Also, the active ingredients can be used very successfully in the ultra-low-volume method (ULV), it being possible to apply formulations with over 95% by weight of active ingredient, or even the active ingredient without additions.

Various types of oils, or herbicides, fungicides, other pesticides, bactericides, may be added to the active ingredients, if appropriate also only immediately prior to use (tank mix). These agents can be admixed with the agents according to the invention in a weight ratio of 1:10 to 10:1.

In the use form as fungicides, the agents according to the invention may also be present together with other active ingredients, for example with herbicides, insecticides, growth regulators, fungicides, or else with fertilizers. Mixing the compounds I or the compositions comprising them in their use form as fungicides with other fungicides frequently results in a broadened fungicidal spectrum of action.

The following list of fungicides together with which the compounds according to the invention can be used is intended to illustrate the possible combinations, but not to impose any limitation:

sulfur, dithiocarbamates, and their derivatives, such as iron (III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfides [sic], ammonia complex of zinc (N,N-ethylenebisdithiocarbamate), ammonia complex of zinc (N,N'- propylenebisdithiocarbamate), zinc (N,N'-propylenebisdithiocarbamate), N,N'-polypropylenebis(thiocarbamoyl)disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenylisopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(2-furyl)-benzimidazole, 2-(4-thiazolyl)benzimidazole, N-(1,1,2,2-tetrachloroethylthio)tetrahydrophthalimide, N-tri-chloromethylthiotetrahydrophthalimide, N-trichloromethylthiophthalimide;

N-dichlorofluoromethylthio-N',N'-dimethyl-N-phenylsulfodiamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene;

strobilurins such as methyl E-methoxyimino-[α-(o-tolyloxy)-o-tolyl]acetate, methyl E-2-{2-[6-(2-cyanophenoxy)pyrimidin-4-yloxy]phenyl}-3-methoxyacrylate, N-methyl-E-methoxyimino-[α-(2-phenoxyphenyl)]acetamide, N-methyl-E-methoxyimino-[α-(2,5-dimethylphenoxy)-o-tolyl]acetamide, methyl E-2-{2-[(2-trifluoromethylpyridyl-6-)oxymethyl]phenyl}-3-methoxyacrylate, methyl (E,E)-methoximino-{2-[1-(3-trifluoromethylphenyl)ethylideneaminooxymethyl]phenyl}acetate, methyl N-(2-{[1-(4-chlorophenyl)-1H-pyrazol-3-yl]oxymethyl}phenyl)-N-methoxycarbamate, anilinopyrimidines such as N-(4,6-dimethylpyrimidin-2-yl)aniline, N-[4-methyl-6-(1-propynyl)pyrimidin-2-yl]aniline, N-[4-methyl-6-cyclopropylpyrimidin-2-yl]aniline;

phenylpyrroles such as 4-(2,2-difluoro-1,3-benzodioxol-4-yl)pyrrole-3-carbonitrile;

cinnamamides such as 3-(4-chlorophenyl)-3-(3,4-dimethoxy-phenyl)acryloylmorpholine;

and a variety of fungicides such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)alanine methyl ester, N-(2,6-dimethylphenyl)-N-chloroacetyl-D,L-2-amino-butyrolactone, DL-N-(2,6-dimethylphenyl)-N-(phenylacetyl)-alanine methyl ester, 5-methyl-5-vinyl-3-(3,5-dichlorophenyl)-2,4-dioxo-1,3-oxazolidine, 3-[3,5-dichlorophenyl-(5-methyl-5-methoxymethyl]-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoro-methyl-3-chloro-2-aminopyridine, 1-((bis(4-fluorophenyl)methylsilyl)methyl)-1H-1,2,4-triazole.

The invention will now be illustrated in greater detail with reference to the examples which follow.

USE EXAMPLES

The fungicidal action of the compounds of the formula I was demonstrated by the following experiments:

The active compounds were formulated separately or jointly as a 10% strength emulsion in a mixture of 94% by weight of cyclohexanone, 4% by weight of Nekanil® LN (Lutensol® AP6, wetting agent having emulsifying and dispersing action based on ethoxylated alkylphenols) and 2% by weight of Wettol® EM (nonionic emulsifier based on ethoxylated castor oil) and diluted with water to give the desired concentration.

Use Example 1

Activity Against Eyespot of Wheat Caused by *Pseudocercosporella herpotrichoides*

Leaves of potted wheat seedlings cv. "Monopol" were sprayed to run off point at the two-leaf stage with an aqueous preparation of active compound which had been prepared from a stock solution of 10% of active compound, 85% of cyclohexanone and 5% of emulsifier. The next day, the test plants were inoculated with an aqueous spore suspension of *Pseudocercosporella herpotrichoides*, the eyespot pathogen, and then cultivated in a greenhouse at 14-16° C. and an atmospheric humidity between 80 and 90% for about 40 days. The extent of the development of the disease at the base of the stem was then determined visually in percent infection.

The plants which had been treated with 250 ppm of active compounds I.1 to I.4 showed an infection of from 0 to 10%, while the untreated plants were 100% infected.

In a further experiment, the plants which had been treated with 63 ppm of active compounds I.1 to I.4 showed an infection of from 0 to 25%, while the untreated plants were 100% infected.

We claim:

1. A method for controlling *Pseudocercosporella herpotrichoides* in crop plants comprising applying to said crop plants an effective amount of benzophenones of the formula I

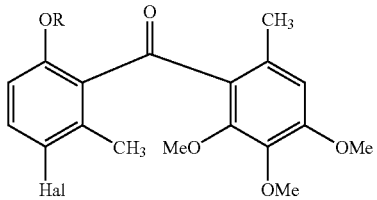

I in which

R is hydrogen or $C_1$-$C_4$-alkyl and

Hal is fluorine, chlorine or bromine.

2. The method as claimed in claim 1, wherein an effective amount of 5-bromo-2', 6-dimethyl-2,4',5',6'-tetramethoxybenzophenone is applied.

3. A method for controlling *Pseudocercosporella herpotrichoides* in wheat and barley comprising applying to said wheat and barley an effective amount of the benzophenones defined in claim 1.

4. The method as claimed in claim 3, wherein an effective amount of 5-bromo-2', 6-dimethyl-2,4',5',6' tetramethoxybenzophenone is applied.

* * * * *

UNITED STATES PATENT AND TRADEMARK OFFICE
CERTIFICATE OF CORRECTION

PATENT NO. : 7,846,958 B2  
APPLICATION NO. : 10/616950  
DATED : December 7, 2010  
INVENTOR(S) : Gewehr et al.

Page 1 of 1

It is certified that error appears in the above-identified patent and that said Letters Patent is hereby corrected as shown below:

In claim 1, col. 8, indicated line 2:
"R is hydrogen or" should read >>R is<<

Signed and Sealed this
Twelfth Day of April, 2011

David J. Kappos
*Director of the United States Patent and Trademark Office*